United States Patent
Motomura et al.

(10) Patent No.: US 8,501,646 B2
(45) Date of Patent: Aug. 6, 2013

(54) NON-WOVEN FABRIC LAMINATE

(75) Inventors: Shigeyuki Motomura, Chiba (JP); Kenichi Suzuki, Ichihara (JP); Kazuhiko Masuda, Chiba (JP); Hisashi Morimoto, Ichihara (JP); Naosuke Kunimoto, Yokkaichi (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 640 days.

(21) Appl. No.: 12/529,485

(22) PCT Filed: Feb. 27, 2008

(86) PCT No.: PCT/JP2008/053358
§ 371 (c)(1),
(2), (4) Date: Sep. 1, 2009

(87) PCT Pub. No.: WO2008/108238
PCT Pub. Date: Sep. 12, 2008

(65) Prior Publication Data
US 2010/0105273 A1    Apr. 29, 2010

(30) Foreign Application Priority Data

Mar. 2, 2007  (JP) ................. 2007-053410

(51) Int. Cl.
  *D04H 3/00*  (2012.01)
  *D04H 1/00*  (2006.01)

(52) U.S. Cl.
  USPC ......... 442/353; 442/329; 442/361; 442/362; 442/364; 442/382

(58) Field of Classification Search
  USPC ......... 442/327, 334–337, 352–353, 361–364
  See application file for complete search history.

(56) References Cited

U.S. PATENT DOCUMENTS

| | | | |
|---|---|---|---|
| 4,551,378 A * | 11/1985 | Carey, Jr. ............... | 428/198 |
| 5,470,639 A | 11/1995 | Gessner et al. | |
| 5,543,206 A | 8/1996 | Austin et al. | |
| 7,585,796 B2 | 9/2009 | Suzuki et al. | |
| 7,674,734 B2 | 3/2010 | Suzuki et al. | |
| 7,884,259 B2 * | 2/2011 | Hanao et al. ........... | 604/358 |
| 2003/0162458 A1 | 8/2003 | Tsujiyama et al. | |
| 2004/0063369 A1 * | 4/2004 | Ahn et al. ............... | 442/327 |
| 2004/0067709 A1 * | 4/2004 | Kishine et al. ......... | 442/327 |
| 2004/0067710 A1 * | 4/2004 | Tsujiyama et al. ..... | 442/329 |
| 2006/0141883 A1 | 6/2006 | Nishiguchi et al. | |
| 2010/0093244 A1 | 4/2010 | Motomura et al. | |

FOREIGN PATENT DOCUMENTS

| | | |
|---|---|---|
| JP | 7-503502 A | 4/1995 |
| JP | 9-512313 A | 12/1997 |
| JP | 11-061624 | 3/1999 |
| JP | 2002-242069 A | 8/2002 |
| JP | 2003-013354 A | 1/2003 |
| JP | 2003-073967 | 3/2003 |
| JP | 2003-096653 A | 4/2003 |
| JP | 2004-197291 A | 7/2004 |
| JP | 2004-244791 A | 9/2004 |
| JP | 2006-112025 A | 4/2006 |
| WO | WO 96/16216 A1 | 5/1996 |
| WO | WO 02/061192 A1 | 8/2002 |
| WO | WO 2006/057369 | 6/2006 |

OTHER PUBLICATIONS

Textile Glossary, definition of spunbond and filament, Celanese Acetate, copyright 2001.*
Filament, Textile Glossary, copyright 2001, Celanese Acetate.*
Fiber, Textile Glossary, copyright 2001, Celanese Acetate.*
Spunbond, Textile Glossary, copyright 2001, Celanese Acetate.*
International Search Report of Application No. PCT/JP2008/053358 dated May 27, 2008.
International Search Report issued in PCT/JP2008/053324, Apr. 22, 2008, Japanese Patent Office, JP (1 page), and English-language translation thereof (1 page).
Official Action issued in U.S. Appl. No. 12/529,474, Mar. 15, 2012, U.S. Patent and Trademark Office, Alexandria, VA (7 pages).
Official Action issued in U.S. Appl. No. 12/529,474, Jul. 9, 2012, U.S. Patent and Trademark Office, Alexandria, VA (6 pages).
Office Action issued in corresponding Korean Patent Application No. 10-2012-7025961 dated Nov. 9, 2012.

* cited by examiner

*Primary Examiner* — Jennifer A Steele
(74) *Attorney, Agent, or Firm* — Buchanan Ingersoll & Rooney PC

(57) ABSTRACT

A non-woven fabric laminate that is excellent in strechability, flexibility, and bulkiness, and that is less sticky and is suitable for a mechanical fastening female material. The non-woven fabric laminate includes a mixed fiber spunbonded non-woven fabric and a non-woven fabric comprising a crimped fiber that is laminated on at least one face of the mixed fiber spunbonded non-woven fabric, which includes a continuous fiber of a thermoplastic elastomer (A) in the range of 10 to 90% by weight and a continuous fiber of a thermoplastic resin (B) in the range of 90 to 10% by weight (where (A)+(B) =100% by weight). The non-woven fabric laminate can be suitably used for a sanitary material and other materials. More specifically, there can be mentioned for instance an absorbent article such as a disposable diaper and a menstrual sanitary product as a sanitary material.

6 Claims, No Drawings

NON-WOVEN FABRIC LAMINATE

TECHNICAL FIELD

The present invention relates to a non-woven fabric laminate that is excellent in stretchability, flexibility, and bulkiness, and that is less sticky and is suitable for a mechanical fastening female material, and relates to an application thereof.

BACKGROUND ART

In recent years, a non-woven fabric has been extensively used for many kinds of applications since it is excellent in air permeability and flexibility. Consequently, many kinds of characteristic properties corresponding to the applications are required for the non-woven fabric, and the characteristic properties are also required to be improved.

For instance, water resistance and excellent moisture permeability are required for a non-woven fabric that is used for a sanitary material such as a paper diaper and a sanitary napkin, a disposable protective cloth such as a medical gown and a work gown, and a base cloth of a fomentation. In addition, stretchability, section to which the non-woven fabric is used. Consequently, a unidirectional stretching laminate having a great number of creases is proposed for the requirements. The unidirectional stretching laminate is prepared by aligning rubber threads in a stretched state at arbitrary intervals, disposing and bonding the rubber thread between inflexible non-woven fabrics, and unloosening the stretched state. However, the great number of creases may cause flexibility to be deteriorated.

As a method for imparting stretchability to a non-woven fabric, there are proposed for instance a method in which a thermoplastic elastomer is used as a raw material of a spunbonded non-woven fabric (Patent document 1: National Publication of International Patent No. 7-503502 for instance) and a method in which a mixed fiber comprising thermoplastic polyurethane and thermoplastic polymer is used as a fiber for forming a non-woven fabric (Patent document 2: Japanese Patent Laid-Open Publication No. 2004-244791 for instance). Moreover, although an object is different from imparting stretchability, there are proposed for instance a long-fiber non-woven fabric that is prepared by combining an adhesive fiber comprising a hydrogenated styrene block copolymer and the like and a non-adhesive fiber, or the like (Patent document 3: Japanese Patent Laid-Open Publication No. 2004-197291 for instance) and a composite non-woven fabric comprising a close contact extensible non-woven fabric layer (Patent document 4: National Publication of International Patent No. 9-512313 for instance).

However, even in the case in which a thermoplastic elastomer is used as a part of raw materials to impart stretchability to a non-woven fabric, the performance cannot be fully displayed in the case in which a laminated material inhibits the stretchability of the non-woven fabric. In addition, a great number of creases may be generated in an obtained laminate in some cases.

On the other hand, a mechanical fastening tape is joined to a diaper, a protective cloth, or the like to make a size thereof fit to a wearer. In the case in which a mechanical fastening tape having a relatively large area is used in such an application in order to enlarge a scope of application for a wearer, a joined section and therefore an obtained member may be hardened.

Patent document 1: National Publication of International Patent No. 7-503502
Patent document 2: Japanese Patent Laid-Open Publication No. 2004-244791
Patent document 3: Japanese Patent Laid-Open Publication No. 2004-197291
Patent document 4: National Publication of International Patent No. 9-512313

DISCLOSURE OF THE INVENTION

Problems to be Solved by the Invention

An object of the present invention is to develop a non-woven fabric laminate that is excellent in stretchability, flexibility, and bulkiness, and that is less sticky and is suitable for a mechanical fastening female material.

Means for Solving the Problems

The present invention provides a non-woven fabric laminate comprises a mixed fiber spunbonded non-woven fabric and a non-woven fabric comprising a crimped fiber laminated on at least one face of the mixed fiber spunbonded non-woven fabric, which comprises a continuous fiber of a thermoplastic elastomer (A) in the range of 10 to 90% by weight and a continuous fiber of a thermoplastic resin (B) in the range of 90 to 10% by weight (where (A)+(B)=100% by weight). The present invention also provides an application of the non-woven fabric laminate.

Effect of the Invention

The non-woven fabric laminate of the present invention is provided with excellent stretchability, flexibility, and bulkiness, less sticky, and performance for a mechanical fastening female material.

BEST MODE OF CARRYING OUT THE INVENTION

Thermoplastic elastomer (A)

As a thermoplastic elastomer (A) that is one of components forming a mixed fiber spunbonded non-woven fabric that constitutes the non-woven fabric laminate of the present invention, many kinds of publicly known thermoplastic elastomers may be used. Further, at least two kinds of the thermoplastic elastomers may also be used in combination.

As the thermoplastic elastomer (A), there can be mentioned for instance a styrene based elastomer that is represented by a block copolymer comprising a polymer block of at least one conjugated diene compound such as butadiene and isoprene and a polymer block of at least one aromatic vinyl compound such as styrene as represented by a polystyrene-polybutadiene-polystyrene block copolymer (referred to as SBS), a polystyrene-polyisoprene-polystyrene block copolymer (referred to as SIS), or a polystyrene-polyethylene.butylene-polystyrene block copolymer (referred to as SEBS) and a polystyrene-polyethylene.propylene polystyrene block copolymer (referred to as SEPS) that is a hydrogenation product thereof, or its hydrogenation product; a polyester based elastomer that is represented by a block copolymer comprising a high crystalline aromatic polyester and a noncrystalline aliphatic polyether; a polyamide based elastomer that is represented by a block copolymer comprising a crystalline polyamide having a high melting point and a noncrystalline polyether or polyester having a low glass transition temperature (Tg); a thermoplastic polyurethane based elastomer that is represented by a block copolymer in which a hard segment comprises polyurethane and a soft segment comprises polycarbonate based polyol, ether based polyol, caprolactone based polyester, adipate based polyester, or the like; a polyolefin based elastomer that is obtained by singly using a noncrystalline or low crystalline ethylene.α-olefin random copolymer, a propylene.α-olefin random copolymer, a propylene.ethylene.α-olefin random copolymer or the like, by mixing the noncrystalline or low crystalline random copolymer and a propylene homopolymer, or by mixing the noncrystalline or low crystalline random copolymer and a crystalline polyolefin such as a copolymer of propylene and a small amount of α-olefin, high density polyethylene, and medium density polyethylene; a polyvinyl chloride based elastomer; a fluorine based elastomer; and the like.

As the styrene based elastomer, there can be mentioned for instance a diblock copolymer and a triblock copolymer based on a polystyrene block and a butadiene rubber block or an isoprene rubber block. The rubber block may also be unsaturated or completely hydrogenated. The styrene based elastomer is specifically manufactured and marketed under trade names, such as KRATON polymer (trade name, manufactured by Shell Chemicals Ltd.), SEPTON (trade name, manufactured by KURARAY CO., LTD.), TUFTEC (trade name, manufactured by Asahi Kasei Corporation), and LEOSTOMER (trade name, manufactured by RIKEN TECHNOS CORPORATION).

The polyester based elastomer is specifically manufactured and marketed under trade names, such as HYTREL (trade name, manufactured by E. I. du Pont de Nemours & Company (Inc.)) and PELPRENE (trade name, manufactured by TOYOBO CO., LTD.).

The polyamide based elastomer is specifically manufactured and marketed under trade names, such as PEBAX (trade product name, manufactured by ATOFINA JAPAN Co., LTD.).

As the polyolefin based elastomer, there can be mentioned for instance an ethylene/α-olefin copolymer and a propylene/α-olefin copolymer. The polyolefin based elastomer is specifically manufactured and marketed under trade names, such as TAFMER (trade name, manufactured by Mitsui Chemicals, Inc.), Engage which is an ethylene-octene copolymer (trade name, manufactured by DuPontDow Elastomers), CATALLOY including a crystalline olefin copolymer (trade name, manufactured by Montel), and Vistamaxx (trade name, manufactured by ExxonMobil Chemical Company).

The polyvinyl chloride based elastomer is specifically manufactured and marketed under trade names, such as Leonyl (trade name, manufactured by RIKEN TECHNOS CORPORATION) and POSMYL (trade name, manufactured by Shin-Etsu Polymer Co., Ltd.).

Among the above thermoplastic elastomers, the thermoplastic polyurethane based elastomer is preferable from the viewpoint of stretchability and processability.

Thermoplastic Polyurethane Based Elastomer

Among the thermoplastic polyurethane based elastomers, a thermoplastic polyurethane based elastomer having a solidification starting temperature of not less than 65° C., preferably not less than 75° C., most preferably not less than 85° C. is preferable. The upper limit of the solidification starting temperature is preferably 195° C. Here, the solidification starting temperature is a value that is measured by using a differential scanning calorimeter (DSC). The solidification starting temperature is a starting temperature of an exothermic peak that is derived from solidification of the thermoplastic polyurethane based elastomer, which occurs when the thermoplastic polyurethane based elastomer is heated up to 230° C. at a rate of 10° C./min, maintained at 230° C. for 5 minutes, and cooled at a rate of 10° C./min. In the case in which the solidification starting temperature is not less than 65° C., a forming defect such as a fusion bonding of fibers, a thread breakage, and a resin block can be suppressed when a mixed fiber spunbonded non-woven fabric is obtained. In addition, a mixed fiber spunbonded non-woven fabric formed can be prevented from winding around an emboss roller in a thermal embossing. Moreover, a mixed fiber spunbonded non-woven fabric obtained is less sticky, and is suitably used for a material that comes into contact with a skin such as a clothing material, a sanitary material, and a sports material. On the other hand, the forming processability can be improved by setting the solidification starting temperature to 195° C. or less. The solidification starting temperature of the formed fiber tends to be higher than that of the thermoplastic polyurethane based elastomer used for forming the fiber.

In order to adjust the solidification starting temperature of the thermoplastic polyurethane based elastomer to not less than 65° C., it is necessary to select compounds that have an optimum chemical structure for each of a polyol, an isocyanate compound, and a chain extender and that are used as a raw material of the thermoplastic polyurethane based elastomer, and to adjust an amount of a hard segment. Here, the amount of a hard segment is a value of percent by weight (% by weight) that is obtained by dividing a total weight of an isocyanate compound and a chain extender used for producing the thermoplastic polyurethane based elastomer with a total amount of a polyol, an isocyanate compound, and a chain extender, and by multiplying the divided value by 100. The amount of a hard segment is preferably in the range of 20 to 60% by weight, more preferably in the range of 22 to 50% by weight, most preferably in the range of 25 to 48% by weight.

The number of particles of insolubles in polar solvents in the thermoplastic polyurethane based elastomer is preferably three millions/g or less, more preferably two and half millions/g or less, further more preferably two millions/g or less. Here, the insolubles in polar solvents in the thermoplastic polyurethane based elastomer is mainly a block object such as a fish eye and gel that are generated during a production of the thermoplastic polyurethane based elastomer. The block object is a component such as a component that is derived from a hard segment aggregate of the thermoplastic polyurethane based elastomer and a component in which a hard segment and/or a soft segment are cross-linked by an allophanate linkage or a bullet linkage or the like, which is generated by a chemical reaction of a raw material that constitutes the thermoplastic polyurethane based elastomer and a chemical reaction between the raw materials.

The number of particles of insolubles in polar solvents is a value that is obtained by measuring insolubles of when the thermoplastic polyurethane based elastomer is dissolved in a dimethylacetamide solvent (hereafter referred to as "DMAC"), by use of a particle size distribution measuring apparatus in which the pore electrical resistance method is adopted and an aperture of 100 μm is mounted. In the case in which the aperture of 100 μm is mounted, the number of particles of 2 to 60 μm in terms of uncross-linked polystyrene can be measured.

In the case in which the number of particles of insolubles in polar solvents is three millions or less relative to the thermoplastic polyurethane based elastomer of 1 g, problems such as an increase in a distribution of a fiber diameter and a thread breakage in spinning can be more effectively suppressed in the range of the solidification starting temperature of the thermoplastic polyurethane based elastomer. From the viewpoint of the suppression of an inclusion of an air bubble into a strand and an occurrence of a thread breakage during a forming of a non-woven fabric with a large spunbond forming machine, the moisture value of the thermoplastic polyurethane based elastomer is preferably 350 ppm or less, more preferably 300 ppm or less, most preferably 150 ppm or less.

In the case in which an endothermic peak is observed by carrying out a thermal analysis for the thermoplastic polyurethane based elastomer using a differential scanning calorimeter (DSC), from the viewpoint of stretchability, a total sum (a) of a heat of fusion that is obtained from an endothermic peak in which a peak temperature is in the range of 90 to 140° C. and a total sum (b) of a heat of fusion that is obtained from an endothermic peak in which a peak temperature is in the range of more than 140 to not more than 220° C., preferably satisfy the following formula (I):

$$a/(a+b) \leq 0.8 \quad \text{(I)};$$

more preferably satisfy the following formula (II):

$$a/(a+b) \leq 0.7 \quad \text{(II); and}$$

most preferably satisfy the following formula (III):

$$a/(a+b) \leq 0.55 \quad \text{(III)}.$$

Here, "a/(a+b)" represents a ratio of heat of fusion (unit: %) of a hard domain of the thermoplastic polyurethane based elastomer. In the case in which the ratio of heat of fusion of a hard domain of the thermoplastic polyurethane based elastomer is 80% or less, the strength and stretchability of a fiber, in particular, a fiber and a non-woven fabric in the mixed fiber spunbonded non-woven fabric are improved. In the present invention, it is preferable that the lower limit of the ratio of heat of fusion of a hard domain of the thermoplastic polyurethane based elastomer is approximately 0.1%.

From the viewpoint of the suppression for an occurrence of a thread breakage, the thermoplastic polyurethane based elastomer preferably has a melting viscosity of 100 to 3000 Pa·s, more preferably 200 to 2000 Pa·s, most preferably 1000 to 1500 Pa·s under the conditions of a temperature of 200° C. and a shear rate of 100 sec$^{-1}$. Here, the melt viscosity is a value that is measured by CAPILOGRAPH (manufactured by TOYO SEIKI Co., Ltd., the length is 30 mm and the diameter is 1 mm for a nozzle).

The mixed fiber spunbonded non-woven fabric that is formed by using the thermoplastic polyurethane based elastomer is excellent in tactile sensation and therefore can be suitably used for a sanitary material or the like.

The thermoplastic polyurethane based elastomer including less insolubles in polar solvents hardly occurs clogging of a filter that is mounted inside an extruder in order to filter impurities or the like, during a production of the mixed fiber spunbonded non-woven fabric. The frequency of an adjustment and a maintenance for equipment is thereby reduced. Consequently, the thermoplastic polyurethane based elastomer that is obtained by carrying out a polymerization reaction of a polyol, an isocyanate compound, and a chain extender and filtrating the resultant is industrially preferable, as described later.

The thermoplastic polyurethane based elastomer including less insolubles in polar solvents can be obtained by carrying out a polymerization reaction of a polyol, an isocyanate compound, and a chain extender and filtrating the resultant, as described later.

Polyolefin Based Elastomer

Among polyolefin based elastomers, a noncrystalline or low crystalline ethylene.α-olefin copolymer that is a copolymer of ethylene and at least one kind of α-olefin having 3 to 20 carbon atoms such as propylene, 1-butene, 1-pentene, 1-hexene, 4-methyl-1-pentene, 1-heptene, 1-octene, and 1-decene, and a noncrystalline or low crystalline propylene.α-olefin copolymer that is a copolymer of propylene and at least one kind of α-olefin having 2 to 20 carbon atoms (not including the number of carbons of 3) such as ethylene, 1-butene, 1-pentene, 1-hexene, 4-methyl-1-pentene, 1-heptene, 1-octene, and 1-decene, whose degree of crystallinity that is measured by an X-ray diffraction is preferably 20% or less (including 0%), are preferable. Moreover, the polyolefin based elastomer can also include, in a small amount, cyclic olefin such as norbornene, 5-methyl norbornene, 5-ethyl norbornene, cyclopentene, 3-methyl cyclopentene, and 4-methyl cyclopentene; cyclic diene such as 5-ethylidene-2-norbornene, 5-methylene-2-norbornene, 1,3-cyclopentadiene, 1,3-cyclohexadiene, and 1,4-cyclohexadiene; or a vinyl compound such as vinyl acetate and methacrylic ester, in addition to the α-olefin. (In the case in which the above polyolefin is a copolymer, a constitutional unit comprising a monomer described first is a main component of the copolymer.)

As the noncrystalline or low crystalline ethylene.α-olefin copolymer, there can be specifically mentioned for instance an ethylene.propylene random copolymer and an ethylene.1-butene random copolymer. The melt flow rate (MFR) of the ethylene.α-olefin copolymer is not restricted in particular providing a spinning property is exhibited. The MFR (ASTM D1238, 230° C., a load of 2160 g) is generally in the range of 1 to 1000 g/10 minutes, preferably 5 to 500 g/10 minutes, more preferably 10 to 100 g/10 minutes.

As the noncrystalline or low crystalline propylene.α-olefin copolymer, there can be specifically mentioned for instance a propylene.ethylene random copolymer, a propylene.ethylene.1-butene random copolymer, and a propylene.1-butene random copolymer. The melt flow rate (MFR) of the propylene.α-olefin copolymer is not restricted in particular providing the spinnability is exhibited. The MFR (ASTM D1238, 230° C., a load of 2160 g) is generally in the range of 1 to 1000 g/10 minutes, preferably 5 to 500 g/10 minutes, more preferably 10 to 100 g/10 minutes.

The polyolefin based elastomer may be the noncrystalline or low crystalline polymer as described above singly. However, the polyolefin based elastomer may also be a composition in which a propylene homopolymer, a copolymer of propylene and a small amount of α-olefin, or crystalline polyolefin such as high density polyethylene and medium density polyethylene is mixed with the noncrystalline or crystalline polymer in an amount of 1 to 40% by weight.

A composition that is preferable as the polyolefin based elastomer in particular is an elastomer composition comprising a polypropylene resin composition that comprises isotactic polypropylene (i): 1 to 40% by weight and a propylene.ethylene.α-olefin copolymer (ii) (a copolymer of propylene of 45 to 89 mole %, ethylene of 10 to 25 mole %, and α-olefin having 4 to 20 carbon atoms) (the amount of copolymerized α-olefin having 4 to 20 carbon atoms dose not exceed 30 mole %): 60 to 99 parts by weight.

Thermoplastic Resin (B)

As a thermoplastic resin (B) that is a raw material of the long continuous fiber comprising the thermoplastic resin other than (A) that is one of components forming the mixed fiber spunbonded non-woven fabric and constitutes the non-woven fabric laminate of the present invention, many kinds of publicly known thermoplastic resins other than the thermoplastic elastomer (A) can be used. There can be mentioned for instance a crystalline polymer having a melting point (Tm) of not less than 100° C. and a noncrystalline polymer having a glass transition temperature of not less than 100° C. Among the thermoplastic resins (B), a crystalline thermoplastic resin is preferable.

Moreover, among the thermoplastic resins (B), the preferred is a thermoplastic resin (an extensible thermoplastic resin) that may gives a non-woven fabric that can be obtained by a production according to a method for producing a publicly known spunbonded non-woven fabric and that has characteristics hardly involving an elastic recovery and a maximum point extension percentage of not less than 50%, preferably not less than 70%, more preferably not less than 100%. In the case in which such a thermoplastic resin (an extensible thermoplastic resin) is used, a mixed fiber spunbonded non-woven fabric that is obtained by combination with a continuous fiber of the thermoplastic elastomer (A) and a non-woven fabric laminate that is obtained by laminating the mixed fiber spunbonded non-woven fabrics exhibit bulkiness by a stretching process. In addition, the tactile sensation can be improved and the elongation arrest function can be imparted to the non-woven fabric laminate. The maximum point extension percentage is an elongation in the machine direction (MD) and/or in the crosswise direction (CD) for the spunbonded non-woven fabric. Although the upper limit of the maximum point extension percentage of the spunbonded non-woven fabric comprising the thermoplastic resin (B) is not necessarily restricted, the upper limit of the maximum point extension percentage is generally 300% or less.

As the thermoplastic resin (B), there can be specifically mentioned for instance polyolefin, for instance, a homopolymer or a copolymer of α-olefin such as ethylene, propylene, 1-butene, 1-hexene, 4-methyl-1-pentene, and 1-octene, such as high pressure low density polyethylene, linear low density polyethylene (so-called LLDPE), high density polyethylene (so-called HDPE), polypropylene (propylene homopolymer), a polypropylene random copolymer, poly-1-butene, poly-4-methyl-1-pentene, an ethylene.propylene random copolymer, an ethylene.1-butene random copolymer, and a propylene.1-butene random copolymer, polyester (such as polyethylene terephthalate, polybutylene terephthalate, and polyethylene naphthalate), polyamide (such as nylon-6, nylon-66, polymetaxylene adipamide), polyvinyl chloride, polyimide, an ethylene.vinyl acetate copolymer, an ethylene.vinyl acetate.vinyl alcohol copolymer, an ethylene.(meta) acrylic acid copolymer, an ethylene-acrylic ester-carbon monoxide copolymer, polyacrylonitrile, polycarbonate, polystyrene, ionomer, and a mixture thereof. Among them, high pressure low density polyethylene, linear low density polyethylene (so-called LLDPE), high density polyethylene, a propylene based polymer such as polypropylene and a polypropylene random copolymer, polyethylene terephthalate, polyamide and the like are more preferable.

Among the thermoplastic resins (B), polyolefin is preferable and a propylene based polymer is particularly preferable, from the viewpoint of stability of a spinning and stretching processability of a non-woven fabric during forming.

As the propylene based polymer, the preferred are a propylene homopolymer having a melting point (Tm) of not less than 155° C., preferably 157 to 165° C., and a copolymer of propylene and a very small amount of one kind or at least two kinds of α-olefins having not less than 2 carbon atoms (not including the number of carbons of 3), preferably 2 to 8 carbon atoms (not including the number of carbons of 3), such as ethylene, 1-butene, 1-pentene, 1-hexene, 1-octene, and 4-methyl-1-pentene.

The melt flow rate (MFR: ASTMD-1238, 230° C., a load of 2160 g) of the propylene based polymer is not restricted in particular providing a melt spinning can be carried out. The MFR is generally in the range of 1 to 1000 g/10 minutes, preferably 5 to 500 g/10 minutes, more preferably 10 to 100 g/10 minutes. The ratio Mw/Mn of the weight average molecular weight (Mw) and the number average molecular weight (Mn) of the propylene based polymer in accordance with the present invention is generally in the range of 1.5 to 5.0. From the viewpoint that a fiber having a satisfactory spinnability and particularly excellent fiber strength is obtained, it is preferable that the ratio Mw/Mn is in the range of 1.5 to 3.0. The values of Mw and Mn can be measured by using a gel permeation chromatography (GPC) according to a publicly known method.

An olefin based polymer composition in which a small amount of HDPE is added to a propylene based polymer is preferable in the viewpoint that the stretching process suitability of a non-woven fabric laminate to be obtained is further improved. From the viewpoint of the spinnability and the stretching processability, the amount of HDPE to be added is preferably in the range of 1 to 20% by weight, more preferably 2 to 15% by weight, further more preferably 4 to 10% by weight to the total 100% by weight of the propylene based polymer and HDPE.

The HDPE to be added to a propylene based polymer is not restricted in particular. However, the density thereof is generally in the range of 0.94 to 0.97 $g/cm^3$, preferably 0.95 to 0.97 $g/cm^3$, more preferably 0.96 to 0.97 $g/cm^3$. Moreover, the melt flow rate (MFR: ASTM D-1238, 190° C., a load of 2160 g) of the HDPE is not restricted in particular providing spinnability is exhibited. From the viewpoint of imparting extensibility, the MFR is generally in the range of 0.1 to 100 g/10 minutes, more preferably 0.5 to 50 g/10 minutes, further preferably 1 to 30 g/10 minutes. In the present invention, a satisfactory spinnability represents that thread breakage does not occur during discharge from a spinning nozzle and in a stretching process, and fusion bonding of a filament does not occur.

Additive

In the present invention, a wide variety of stabilizers such as a heat stabilizer and a weathering stabilizer, an antistatic agent, a slip agent, an anti-fogging agent, a lubricant, a dye/a pigment, a natural oil, a synthetic oil, and a wax may be added as an optional component to the mixed fiber spunbonded non-woven fabric as described above and the crimped fiber non-woven fabric that will be described later.

As the stabilizers, there can be mentioned for instance an antiaging agents such as 2,6-di-t-butyl-4-methyl phenol (BHT); phenol based antioxidants such as tetrakis [methylene-3-(3,5-di-t-butyl-4-hydroxyphenyl)propionate]methane, 6-(3,5-di-t-butyl-4-hydroxyphenyl)alkyl ester propionate, 2,2'-oxamidebis[ethyl-3-(3,5-di-t-butyl-4-hydroxyphenyl) propionate, and Irganox 1010 (hindered phenol based antioxidant: trade name); fatty acid metal salts such as zinc stearate, calcium stearate, and calcium 1,2-hydroxystearate; and polyhydric alcohol fatty acid esters such as glycerol monostearate, glycerol distearate, pentaerythritol monostearate, pentaerythritol distearate, and pentaerythritol tristearate. The stabilizer as described above may be used singly, or in combination of at least two kinds of the stabilizers.

Mixed Fiber Spunbonded Non-Woven Fabric

The mixed fiber spunbonded non-woven fabric that constitutes the non-woven fabric laminate of the present invention is a mixed fiber spunbonded non-woven fabric that includes a continuous fiber of the thermoplastic elastomer (A) and a continuous fiber of the thermoplastic resin (B) at a rate of 10 to 90% by weight and 90 to 10% by weight (where (A)+(B) =100% by weight). The mixed fiber spunbonded non-woven fabric preferably has a content of the continuous fiber of the thermoplastic elastomer (A) of not less than 20% by weight, more preferably not less than 30% by weight, from the viewpoint of the strechability and flexibility. On the other hand, the content of the continuous fiber of the thermoplastic elastomer (A) is preferably not more than 70% by weight, more preferably not more than 60% by weight, from the viewpoint of processability (such as a sticky resistant property).

The fiber diameters (average value) of the continuous fiber of the thermoplastic elastomer (A) and the continuous fiber of the thermoplastic resin (B) that form the mixed fiber spunbonded non-woven fabric in accordance with the present invention are generally 50 µm or less, preferably in the range of 5 to 40 µm, more preferably in the range of 7 to 30 µm for each. The fiber diameter of the continuous fiber of the thermoplastic elastomer (A) may be equivalent to or different from that of the continuous fiber of the thermoplastic resin (B).

In an application of a sanitary material such as a diaper, the mixed fiber spunbonded non-woven fabric in accordance with the present invention generally has a mass per unit area of 120 g/m$^2$ or less, preferably 80 g/m$^2$ or less, more preferably 50 g/m$^2$ or less, further more preferably in the range of 40 to 15 g/m$^2$, from the viewpoint of flexibility and air permeability.

In the case in which the mixed fiber spunbonded non-woven fabric in accordance with the present invention is laminated and integrated, many kinds of publicly known confounding methods may be adopted. In the case in which the lamination and integration are carried out off-line, the mixed fiber spunbonded non-woven fabric may be rewound without confounding, in some case. However, a slight pre-bonding may also be carried out by a publicly known confounding method, thereby improving productivity. As such a confounding method, there can be mentioned for instance a method which comprises accumulating fibers on a moving belt and packing the fibers by a nip roller. In this case, it is preferable that the roller is heated so that a slight pre-bonding can be carried out. As a method for carrying out a pre-bonding, in addition to the above, there can be mentioned for instance a method using a means such as a needle punch, a water jet, and ultrasonic waves, a hot embossing method using an embossing roll, and a method using a hot air through. In any methods, confounding lightly than general is preferable from the viewpoint of texture and stretchability after lamination. The above confounding method may be used singly, or in combination of a plurality of confounding methods.

The mixed fiber spunbonded non-woven fabric in accordance with the present invention may be produced by a publicly known method for producing a spunbonded non-woven fabric, for instance a method as disclosed in Japanese Patent Laid-Open Publication No. 2004-244791, using the thermoplastic elastomer (A) and the thermoplastic resin (B).

Specifically, for instance, the thermoplastic elastomer (A) and the thermoplastic resin (B) are molten by separate extrusion machines, respectively, and molten polymers are separately introduced to spinneret (dies) provided with a great number of spinning holes (nozzles). The thermoplastic elastomer (A) and the thermoplastic resin (B) are then independently discharged from different spinning holes at the same time, and the resulting long-continuous fiber of the thermoplastic elastomer (A) and the continuous fiber of the thermoplastic resin (B) by melt spinning are introduced to a cooling chamber. After the continuous fiber of the thermoplastic elastomer (A) and the continuous fiber of the thermoplastic resin (B) are cooled by a cooling air in the cooling chamber, the continuous fibers are stretched (towed) by a stretching air and accumulated on a moving collection face. The mixed fiber spunbonded non-woven fabric in accordance with the present invention is thus produced. The melting temperature of the polymer is not restricted in particular providing the melting temperature is equivalent to or higher than the softening temperature or the fusion temperature of the polymer and less than the thermal decomposition temperature of the polymer and may be determined depending on a polymer to be used. The temperature of the spinneret depends on a polymer to be used, and, for instance, in the case in which a thermoplastic polyurethane based elastomer or an olefin based copolymer elastomer is used as the thermoplastic elastomer (A) and a propylene based polymer or an olefin based polymer composition of a propylene based polymer and HDPE is used as the thermoplastic resin (B), the temperature of the spinneret may generally be set to the range of 180 to 240° C., preferably the range of 190 to 230° C., more preferably the range of 200 to 225° C.

Providing the temperature of a cooling air is a temperature at which the polymer is solidified, the temperature of a cooling air is not restricted in particular, and is generally in the range of 5 to 50° C., preferably 10 to 40° C., more preferably 15 to 30° C. The wind velocity of a stretching air is generally in the range of 100 to 10000 m/min, preferably in the range of 500 to 10000 m/min.

Crimped Fiber Non-Woven Fabric

As the non-woven fabric comprising the crimped fiber in accordance with the present invention, non-woven fabrics comprising many kinds of publicly known crimped fibers may be used. For the crimped fiber, any of a crimped fiber comprising so-called short fiber and a crimped fiber comprising a continuous fiber may be used. A crimped fiber comprising a continuous fiber obtained by a spunbonding method is preferable because of the following reasons: the crimped fiber comprising a continuous fiber hardly occurs a loss of fibers from the crimped fiber non-woven fabric when laminated to the mixed fiber spunbonded non-woven fabric to be a non-woven fabric laminate; the crimped fiber comprising a continuous fiber can be laminated to the mixed fiber spunbonded non-woven fabric in-line; and the crimped fiber comprising a continuous fiber is excellent in quality and productivity.

It is preferable that the crimped fiber that forms the crimped fiber non-woven fabric in accordance with the present invention has a number of crimps of not less than 5/25 mm, more preferably not less than 10/25 mm, particularly preferably in the range of 10 to 70/25 mm, from the viewpoint that the crimped fiber is excellent in an engaging force when used for a mechanical fastening tape, stretching processability (or extensibility), bulkiness, and flexibility.

The fiber diameter of the crimped fiber in accordance with the present invention is generally 50 μm or less, preferably in the range of 5 to 40 μm, more preferably in the range of 7 to 30 μm.

The crimped fiber non-woven fabric in accordance with the present invention generally has a mass per unit area of 120 g/m² or less, preferably 80 g/m² or less, more preferably 50 g/m² or less, further more preferably in the range of 40 to 15 g/m², from the viewpoint of flexibility and air permeability in an application of a sanitary material such as a diaper.

As the crimped fiber in accordance with the present invention, there can be mentioned for instance a crimped fiber in which a crimp is imparted, by a publicly known means such as applying a mechanical stress, to a fiber comprising a single polymer that is selected from the thermoplastic elastomer (A), the thermoplastic resin (B) and others that are raw materials of the mixed fiber spunbonded non-woven fabric; a crimped fiber in which a crimp is imparted by changing a cooling temperature of a side face of a fiber which is subjected to melt spinning; a crimped fiber in which a crimp is imparted by carrying out the melt spinning of a modified cross-section fiber and by controlling a distribution of a degree of crystallinity caused by an anisotropy in cooling or an asymmetry of a cross sectional shape; and a crimped fiber in which a crimp is imparted by producing a composite fiber comprising at least two kinds of polymers, for instance, the thermoplastic elastomer (A), the a thermoplastic resin (B), and the like that have different crystallization temperatures, melting points, softening temperatures, melting viscosities or the like, and utilizing the difference in the above characteristics.

The crimped fiber comprising a composite fiber generally has a fiber structure of an eccentric core-in-sheath crimped fiber or a parallel type crimped fiber. In order to impart a crimp to a composite fiber, many kinds of publicly known methods may be adopted, such as a method in which a crimp is imparted by carrying out a stretch heat treatment of a composite fiber; a method in which a crimp is imparted by carrying out a heat treatment of a composite fiber, for instance, at a temperature of 5 to 30° C. lower than a melting point of a low-melting component without stretching a composite fiber; and a method in which a crimp is imparted by cooling a composite fiber which has been subjected to melt spinning.

It is preferable that the crimped fiber in accordance with the present invention is an eccentric core-in-sheath crimped fiber or a parallel type crimped fiber in which a first component is comprising a propylene.α-olefin copolymer having a melting point (Tm) of 150° C. or less, a second component is comprising a propylene based polymer having a melting point (Tm) of 155° C. or higher, and the ratio (the mass ratio) of the first component to the second component is in the range of 50/50 to 95/5, preferably 60/40 to 90/10, more preferably 70/30 to 90/10.

The eccentric core-in-sheath composite fiber is not restricted in particular unless the core (the center) of the propylene based polymer forming a core section corresponds to a core of a composite fiber. However, it is preferable that the core of the propylene based polymer forming a core section is positioned more distantly from a core of a composite fiber since a crimp easily occurs. Moreover, for the eccentric core-in-sheath composite fiber, the propylene based polymer forming a core section may be partially come to the surface of an eccentric core-in-sheath composite fiber.

The parallel type composite fiber may have a linear or in an arc-shape junction plane of a fiber cross section between the propylene.α-olefin copolymer that forms the first component and the propylene based polymer that forms the second component. In the case in which the junction plane of the fiber cross section is in an arc shape, the junction plane may be circular shape in which the propylene based polymer is inserted into the propylene.α-olefin copolymer or may be in a crescent shape in which the propylene based polymer is concave.

Propylene.α-Olefin Copolymer

In the propylene.α-olefin copolymer that is the first component of the eccentric core-in-sheath crimped fiber or the parallel type crimped fiber and that has a melting point (Tm) of 150° C. or less, the melting point (Tm) is preferably in the range of 120 to 150° C., more preferably in the range of 125 to 147° C. Moreover, the propylene.α-olefin copolymer is a copolymer of propylene and a homopolymer of α-olefin having not less than 2 carbon atoms (not including the number of carbons of 3), preferably in the range of 2 to 8 carbon atoms (not including the number of carbons of 3), such as ethylene, 1-butene, 1-pentene, 1-hexene, 1-octene, and 4-methyl-1-pentene, or is a copolymer of propylene and at least two kinds of the α-olefin. The propylene.α-olefin copolymer is preferably a random copolymer.

By using a propylene.α-olefin copolymer that has a melting point (Tm) in the above range, a crimped non-woven fabric that has a small crimp diameter and that is excellent in bulkiness and flexibility can be obtained. A propylene.α-olefin copolymer that has a melting point (Tm) exceeding the above range shows insufficient crimp, whereby the flexibility of a non-woven fabric to be obtained tends to be reduced. On the other hand, a propylene α-olefin copolymer that has a melting point (Tm) less than the above range shows insufficient crimp, whereby a non-woven fabric to be obtained may be sticky.

The melt flow rate (MFR: ASTM D-1238, 230° C., a load of 2160 g) of the propylene.α-olefin copolymer in accordance with the present invention is not restricted in particular providing a melt spinning can be carried out. The MFR is generally in the range of 1 to 1000 g/10 minutes, preferably 5 to 500 g/10 minutes, more preferably 10 to 100 g/10 minutes. The ratio Mw/Mn of the weight average molecular weight (Mw) and the number average molecular weight (Mn) of the propylene.α-olefin copolymer in accordance with the present invention is generally in the range of 1.5 to 5.0. From the viewpoint that a composite fiber having a satisfactory spinnability and particularly excellent fiber strength is obtained, it is further preferable that the ratio Mw/Mn is in the range of 1.5 to 3.0. In the present invention, a satisfactory spinnability represents that a thread breakage does not occur during discharge from spinning nozzle and in a stretching process, and a fusion bonding of a filament does not occur. In the present invention, the values of Mw and Mn can be measured by using a gel permeation chromatography (GPC) according to a publicly known method.

The melting point (Tm) of the propylene.α-olefin copolymer in accordance with the present invention is measured by using a differential scanning calorimeter (DSC), as follows. A propylene.α-olefin copolymer is heated at a rate of temperature increase of 10° C./min to a temperature approximately 50° C. higher than a temperature that gives an extreme value of a fusion endothermic curve when the temperature is raised at the same rate, is maintained at the temperature for 10 minutes, and is cooled to 30° C. at a rate of temperature decrease of 10° C./min. The propylene.α-olefin copolymer is then heated again at a rate of temperature increase of 10° C./min to a prescribed temperature, and a fusion curve is measured. From the fusion curve, a temperature (Tp) that gives an extreme value of a fusion endothermic curve is obtained according to a method of ASTM D3419. The endothermic peak of the peak temperature is set to the melting point (Tm).

Propylene Based Polymer

The propylene based polymer that is the second component of the eccentric core-in-sheath crimped fiber or the parallel type crimped fiber and that has a melting point (Tm) of 155° C. or higher is preferably a homopolymer of propylene having a melting point (Tm) preferably in the range of 157 to 165° C., or a copolymer, which has a melting point in the above range, of propylene and a very small amount of one or at least two kinds of α-olefins having not less than 2 carbon atoms, preferably in the range of 2 to 8 carbon atoms, such as ethylene, 1-butene, 1-pentene, 1-hexene, 1-octene, and 4-methyl-1-pentene. Of these, a homopolymer of propylene is preferable.

Use of the propylene based polymer that has a rate of crystallization and a melting point (Tm) in the above ranges gives a crimped composite fiber that has a small crimp diameter, which is capable of giving a crimped non-woven fabric excellent in bulkiness and flexibility. A propylene based polymer that has a rate of crystallization exceeding the above range shows insufficient crimp. On the other hand, a propylene based polymer that has a melting point (Tm) less than the above range shows insufficient crimp in some cases.

The melt flow rate of the propylene based polymer in accordance with the present invention (MFR: ASTM D-1238, 230° C., a load of 2160 g) is not restricted in particular providing a melt spinning can be carried out. The MFR is generally in the range of 1 to 1000 g/10 minutes, preferably 5 to 500 g/10 minutes, more preferably 10 to 100 g/10 minutes. The ratio Mw/Mn of the weight average molecular weight (Mw) and the number average molecular weight (Mn) of the propylene based polymer in accordance with the present invention is generally in the range of 1.5 to 5.0. From the viewpoint that a composite fiber having a satisfactory spinnability and particularly excellent fiber strength is obtained, it is more preferable that the ratio Mw/Mn is in the range of 1.5 to 3.0. In the present invention, a satisfactory spinnability represents that thread breakage does not occur during discharge from a spinning nozzle and in a stretching process and fusion bonding of a filament does not occur. In the present invention, the values of Mw and Mn can be measured by using a gel permeation chromatography (GPC) according to a publicly known method.

The melting point (Tm) of the propylene.α-olefin copolymer in accordance with the present invention is measured by using a differential scanning calorimeter (DSC), as follows. A propylene.α-olefin copolymer is heated at a rate of temperature increase of 10° C./min to a temperature approximately 50° C. higher than a temperature that gives an extreme value of a fusion endothermic curve when the temperature is raised at the same rate, is maintained at the temperature for 10 minutes, and is cooled to 30° C. at a rate of temperature decrease of 10° C./min. The propylene.α-olefin copolymer is then heated again at a rate of temperature increase of 10° C./min to a prescribed temperature, and a fusion curve is measured. From the fusion curve, a temperature (Tp) that gives an extreme value of a fusion endothermic curve is obtained according to a method of ASTM D3419. The endothermic peak of the peak temperature is set to the melting point (Tm).

The crimped fiber non-woven fabric in accordance with the present invention may be confounded by many kinds of publicly known confounding methods depending on the application. As such a confounding method, there can be mentioned for instance a method using a means such as a needle punch, a water jet, and ultrasonic waves, a hot embossing method using an embossing roll, and a method of a partial thermal fusion bonding using a hot air through. The confounding method may be used singly, or in the combination of a plurality of confounding methods.

In the case in which a thermal fusion bonding is carried out by a hot embossing method, an emboss area ratio is generally in the range of 5 to 20%, preferably 5 to 10%, and a non-emboss unit area is generally at least 0.5 mm$^2$, preferably in the range of 4 to 40 mm$^2$. The non-emboss unit area is a maximum area of a quadrangle that is inscribed to the emboss in a non-emboss part of a minimum unit enclosed by an emboss part on all four sides. The reason why a spunbonded non-woven fabric having an emboss area ratio and a non-emboss unit area in the above ranges is preferable is that, in particular when the spunbonded non-woven fabric is used as a crimped fiber non-woven fabric, a tying point is formed in an emboss part in which crimped continuous fibers are practically linked to each other, and a continuous fiber crimped between embosses exists with a large degree of freedom in a state that the continuous fiber draws a spiral or is folded, whereby the satisfactory extensibility is more imparted.

In the case in which the emboss area ratio is larger, the extensibility of the crimped fiber non-woven fabric is slightly reduced and the extensible range is reduced, but the sheet strength of a non-woven fabric laminate to be obtained is improved. On the other hand, in the case in which the emboss area ratio is smaller, the sheet strength of a non-woven fabric laminate to be obtained is reduced in some degree, but the extensibility of the crimped fiber non-woven fabric is increased, and the extensible range is enlarged.

A process of a confounding of the crimped fiber non-woven fabric, including a hot embossing, may be carried out before or after laminating the mixed fiber spunbonded non-woven fabric and the crimped fiber non-woven fabric. In the case in which the confounding is carried out after laminating, it is not necessary to carry out the confounding.

Non-Woven Fabric Laminate

The non-woven fabric laminate of the present invention is a laminate comprising a mixed fiber spunbonded non-woven fabric and a non-woven fabric comprising the crimped fiber. The mixed fiber spunbonded non-woven fiber includes a continuous fiber of the thermoplastic elastomer (A) of 10 to 90% by weight and a continuous fiber of the thermoplastic resin (B) of 90 to 10% by weight and the non-woven fabric comprising the crimped fiber is laminated on at least one face of the mixed fiber spunbonded non-woven fabric.

The non-woven fabric laminate of the present invention can be produced by a method in which a mixed fiber spunbonded non-woven fabric and a crimped fiber non-woven fabric that have been obtained in advance is laminated, and can be produced by a method for continuously accumulating a crimped fiber non-woven fabric or a mixed fiber spunbonded non-woven fabric on a mixed fiber spunbonded non-woven fabric that has been obtained in advance or a crimped fiber non-woven fabric that has been obtained in advance.

After laminating the mixed fiber spunbonded non-woven fabric and the crimped fiber non-woven fabric, the mixed fiber spunbonded non-woven fabric and the crimped fiber non-woven fabric may be confounded by many kinds of publicly known confounding methods as needed. As such a confounding method, there can be mentioned for instance a method using a means such as a needle punch, a water jet, and ultrasonic waves, a hot embossing method using an embossing roll, and a method of a partial thermal fusion bonding using a hot air through. In the above bonding, a confounding method may be used singly, or in combination of a plurality of confounding methods.

In the case in which the mixed fiber spunbonded non-woven fabric and the crimped fiber non-woven fabric is confounded by a hot embossing method, it is preferable to carry out a hot embossing under the conditions as described above.

In the non-woven fabric laminate in which the mixed fiber spunbonded non-woven fabric and the crimped fiber non-woven fabric are confounded by a hot embossing method, when the non-woven fabric laminate is stretched, the crimped fiber is extended and the crimp is released. However, when the tensile force is lost, the fiber is folded again in a spiral shape between embosses to be in an almost original state, and the crimp occurs, thereby hardly generating pleats (creases) in the non-woven fabric laminate.

In the case in which the non-woven fabric laminate of the present invention is used for an application of a sanitary material such as a diaper, from the viewpoint of flexibility and air permeability, the mass per unit area of the non-woven fabric laminate is generally 200 $g/m^2$ or less, preferably 100 $g/m^2$ or less, more preferably 80 $g/m^2$ or less, further more preferably in the range of 60 to 15 $g/m^2$ in sum total of the non-woven fabric laminate.

Providing the layer structure of the non-woven fabric laminate of the present invention includes the mixed fiber spunbonded non-woven fabric and the crimped non-woven fabric as a layer that constitutes a laminate, the layer structure is not restricted in particular. In other words, the non-woven fabric laminate of the present invention can adopt many kinds of structures such as not only a two-layer structure of the mixed fiber spunbonded non-woven fabric and the crimped non-woven fabric but also structures of at least three layers, for instance the crimped non-woven fabric/mixed fiber spunbonded non-woven fabric/crimped non-woven fabric, the mixed fiber spunbonded non-woven fabric/crimped non-woven fabric/mixed fiber spunbonded non-woven fabric, and the mixed fiber spunbonded non-woven fabric/mixed fiber spunbonded non-woven fabric/crimped non-woven fabric. Moreover, the laminate of the present invention is not restricted to the above examples, and another layer (intermediate layer) such as a spunbonded non-woven fabric, a melt blow non-woven fabric, and a permeable film may also be disposed between the mixed fiber spunbonded non-woven fabric and the crimped non-woven fabric.

From the viewpoint of the peel strength (peel resistance property) of the laminate, a polyolefin non-woven fabric/film is preferable as the intermediate layer. More specifically, polyolefin equivalent to polyolefin that constitutes the mixed fiber spunbonded non-woven fabric and the crimped non-woven fabric, or polyolefin having a melting point lower than that of the polyolefin that constitutes the mixed fiber spunbonded non-woven fabric and the crimped non-woven fabric is preferable for a surface layer of a fiber that constitutes the non-woven fabric, and a non-woven fabric and a film that are disposed on an outermost layer.

In the case in which the non-woven fabric laminate of the present invention is used for a female material of mechanical fastening, it is preferable the crimped non-woven fabric is disposed on an outermost layer.

The non-woven fabric laminate of the present invention may also comprises another layer laminated on any plane in addition to the mixed fiber spunbonded non-woven fabric and the crimped non-woven fabric.

The above described another laminated layer that constitutes the non-woven fabric laminate of the present invention is not restricted in particular, and many kinds of layers may be laminated depending on an application.

Specifically, there can be mentioned for instance a knitted fabric, a woven fabric, a non-woven fabric, and a film. In the case in which the non-woven fabric laminate of the present invention is laminated (bonded) to another layer, many kinds of publicly known methods may be adopted, such as a thermal fusion bonding method such as a hot embossing and an ultrasonic wave fusion bonding, a mechanical confounding method such as a needle punch and a water jet, a bonding method using an adhesive such as a hot melt adhesive and an urethane based adhesive, and a laminating method with an extrusion laminate.

As a non-woven fabric that is laminated to the non-woven fabric laminate of the present invention, there can be mentioned for instance many kinds of publicly known non-woven fabrics such as a spunbonded non-woven fabric, a melt blow non-woven fabric, a wet non-woven fabric, a dry non-woven fabric, a dry pulp non-woven fabric, a flash spinning non-woven fabric, and an opening non-woven fabric.

As a material that constitutes the non-woven fabric, the many kinds of publicly known thermoplastic resins as described above may be used.

As a film that is laminated to the non-woven fabric laminate of the present invention, there can be mentioned for instance a moisture permeable film and an air permeable film.

Moisture Permeable Film

The moisture permeable film that constitutes the non-woven fabric laminate of the present invention is a film comprising a thermoplastic elastomer (hereafter referred to as a thermoplastic elastomer (A'), which is separated from the thermoplastic elastomer (A) that is included in the mixed fiber spunbonded non-woven fabric layer). The thermoplastic elastomer (A') is a film that generally indicates a moisture permeability of not less than 2000 $g/m^2 \cdot day$, preferably not less than 3000 $g/m^2 \cdot day$, more preferably not less than 4000 $g/m^2 \cdot day$ according to the JIS L1099 A-1 method (under the conditions of 40° C., a relative humidity of 90%, a $CaCl_2$ method) at a film thickness of 30 μm, when the moisture permeability is evaluated.

The thickness of the moisture permeable film in accordance with the present invention may be selected arbitrarily depending on a wide variety of applications, but is generally in the range of 10 to 50 μm, preferably 15 to 40 μm. From the viewpoint of preventing a pin hole in a laminate with a non-woven fabric and maintaining the mechanical strength and the suitable water resistance, the thickness of the moisture permeable film is preferably at least 10 μm. From the viewpoint of obtaining a satisfactory moisture permeability and flexibility, the thickness of the moisture permeable film is preferably 50 μm or less.

The moisture permeable film in accordance with the present invention may be formed by a publicly known film forming method using the thermoplastic elastomer (A'). For instance, the thermoplastic elastomer (A') is molten by an extrusion machine, and a film is then formed by using a T-die or a ring die. However, an elastomer having a moisture permeability is much sticky in general and causes a blocking to occur. Consequently, the thermoplastic elastomer (A') may be extruded on the mixed fiber spunbonded non-woven fabric layer to form a film layer directly or indirectly.

Thermoplastic Elastomer (A')

Providing the thermoplastic elastomer (A') in accordance with the present invention is a thermoplastic elastomer that has a moisture permeability in the case in which a film is formed, a wide variety of thermoplastic elastomers may be used as the thermoplastic elastomer (A') in accordance with the present invention. To confirm that the thermoplastic elastomer (A') has a moisture permeability, for instance, a measuring method according to the JIS L1099 A-1 method (under the conditions of 40° C., a relative humidity of 90%, a CaCl$_2$ method) can be used. When permeability of a moisture vapor is confirmed, the thermoplastic elastomer (A') is judged to have a moisture permeability. In this case, a film that preferably indicates a moisture permeability of not less than 2000 g/m$^2$·day, preferably not less than 3000 g/m$^2$·day, according to the JIS L1099 A-1 method at a film thickness of 30 µm, is be preferably used in the present invention.

As a preferable thermoplastic elastomer for the thermoplastic elastomer (A'), there can be mentioned for instance a polyester based elastomer (A'-1), a polyamide based elastomer (A'-2), and a thermoplastic polyurethane based elastomer (A'-3).

An additive such as an anti-oxidizing agent, a weathering stabilizer, an antistatic agent, an anti-fogging agent, an anti-blocking agent, a lubricant, a nucleating agent, and a pigment, which are generally used, or other copolymers may be compounded to the thermoplastic elastomer (A') as needed without departing from the scope of the present invention.

Polyester Based Elastomer (A'-1)

As a polyester based elastomer (A'-1), there can be mentioned for instance a block copolymer in which a block copolymerization of a hard segment which is a structural unit represented by the following formula (I) derived from aromatic polyester and a soft segment which is a structural unit represented by the following formula (II) derived from aliphatic polyether is carried out.

—O-D-O—CO—R—CO—    (I)

—O-G-O—CO—R—CO—    (II)

In the above formulas, D is a divalent residue in which two hydroxyl groups are excluded from diol having a molecular weight of approximately 250 or less, R is a divalent residue in which two carboxyl groups are excluded from dicarboxylic acid having a molecular weight of approximately 300 or less, and G is a divalent residue in which hydroxyl groups of both terminals are excluded from poly(alkylene oxide)glycol having an average molecular weight in the range of approximately 400 to approximately 3500. Here, the amount of an ethylene oxide group that is inserted in the structural unit represented by the formula (II) that is copolyether ester of poly(alkylene oxide)glycol is generally in the range of approximately 25 to 68 mass % to the total mass of copolyether ester.

In the present invention, it is particularly preferable that the aromatic polyester is tetramethylene terephthalate and the aliphatic polyether is alkylene ether glycol. Specifically, polybutylene terephthalate/polytetramethylene ether glycol block copolymer can be mentioned for instance. Specifically, a commercialized product is manufactured and marketed under the trade names, such as HYTREL (trade name, manufactured by E. I. du Pont de Nemours & Company (Inc.)) and PELPRENE (trade name, manufactured by TOYOBO CO., LTD.).

Polyamide Based Elastomer (A'-2)

As a polyamide based elastomer (A'-2), there can be mentioned for instance a multi block copolymer in which polyamide is used for a hard segment and diol of polyester having a low glass transition temperature or of polyol is used for a soft segment. Here, as the polyamide component, there can be mentioned for instance nylon 6, nylon 66, nylon 610, nylon 11, and nylon 12. Among them, nylon 6 and nylon 12 are preferable. As the polyether diol, there can be mentioned for instance poly(oxytetramethylene)glycol and poly(oxypropylene)glycol. As the polyester diol, there can be mentioned for instance poly(ethylene.1,4-adipate)glycol, poly(butylene.1,4-adipate)glycol, and polytetramethylene glycol. As a specific example, nylon 12/polytetramethylene glycol block copolymer can be mentioned. As a commercialized product, there can be specifically mentioned for instance a polyamide based elastomer that is manufactured and marketed under the trade names, such as DAIAMID (manufactured by Daicel-Hüls Ltd.) and PEBAX (manufactured by Atochem Ltd.) [both of which are brand names].

Thermoplastic Polyurethane Based Elastomer (A'-3)

As a thermoplastic polyurethane based elastomer (A'-3), there can be mentioned for instance a block copolymer in which polyurethane as a hard segment that is obtained by a reaction of short chain polyol (a molecular weight in the range of 60 to 600) and diisocyanate and polyurethane as a soft segment that is obtained by a reaction of long chain polyol (a molecular weight in the range of 600 to 4000) and diisocyanate. As the diisocyanate, toluene diisocyanate and diphenylmethane diisocyanate can be mentioned for instance. As the short chain polyol, there can be mentioned for instance ethylene glycol, 1,3-propylene glycol, and bisphenol A.

As the thermoplastic polyurethane based elastomer (A'-3), there can be mentioned for instance a polymer (polyether polyurethane) which is obtained by addition polymerizing diisocyanate to polylactone ester polyol such as polycaprolactone glycol in the presence of short chain polyol; a polymer (polyester polyurethane) which is obtained by addition polymerizing diisocyanate to adipic acid ester polyol such as poly(ethylene.1,4-adipate)glycol and poly(butylene.1,4-adipate)glycol in the presence of short chain polyol; and a polymer is obtained by addition polymerizing diisocyanate to polytetramethylene glycol that is obtained by a ring opening of tetrahydrofuran in the presence of short chain polyol. As a commercialized product, there can be specifically mentioned for instance a thermoplastic polyurethane based elastomer that is manufactured and marketed under the trade names, such as VULKOLLAN (manufactured by Bayer AG), Chemigum SL (manufactured by Goodyear Tire & Rubber Company), ADIPRENE (manufactured by du Pont de Nemours & Company (Inc.)), and VALCAPLEN (manufactured by Imperial Chemical Industries (ICI)) [which are all brand names].

Among them, the polyester based elastomer (A'-1) and the thermoplastic polyurethane based elastomer (A'-3) are preferable from the viewpoint that they are excellent in moisture permeability. In particular, the thermoplastic polyurethane based elastomer (A'-3) is more preferable from the viewpoint that it has a combination of stretchability and moisture permeability.

Air Permeable Film

An air permeable film in accordance with the present invention is a film comprising a thermoplastic resin (hereafter referred to as a thermoplastic resin (B'), which is separated from the thermoplastic resin (B)). The thermoplastic resin (B') is a film in which a gas such as oxygen and a moisture vapor is permeated and a liquid such as water is hard to be permeated. The thermoplastic resin (B') is a microporous film that generally indicates a moisture permeability in the range of 1000 to 20000 g/m$^2$·24 hrs according to the JIS L1099 A-1 method (under the conditions of 40° C., a relative humidity of 90%, and a CaCl$_2$ method).

Even in the case in which a film (a precursor) in the stage before air permeability is imparted has a moisture permeability of approximately 0 g/m$^2$·24 hrs, the film can be laminated to the mixed fiber spunbonded non-woven fabric to be a non-woven fabric laminate, and an appropriate processing can be carried out to make an air permeable film having a moisture permeability in the above range.

The air permeable film in accordance with the present invention is a thermoplastic resin composition that includes the thermoplastic resin (B'), preferably includes the thermoplastic resin (B') and filler. In the case in which the air permeable film in accordance with the present invention is a resin composition that includes the thermoplastic resin (B') and filler, the compounding amount of filler is more preferably in the range of 30 to 75% by weight, further more preferably 40 to 70% by weight, particularly preferably 40 to 60% by weight (where the total sum of the thermoplastic resin (B') and filler is 100% by weight). The air permeable film in accordance with the present invention can be obtained by stretching, in at least one direction, a film (a precursor) that can be obtained by an extrusion forming of the thermoplastic resin composition.

As a filler, there can be preferably mentioned for instance a cross-linked particle such as a polymethyl methacrylate (PMMA) particle and a polystyrene particle; an organic compound based filler such as a resin that is incompatible with a thermoplastic resin that is used as a film substrate (for instance polyethylene terephthalate or polyamide in the case in which a polyolefin based resin is used); and an inorganic compound based filler such as calcium carbonate, barium sulfate, calcium sulfate, barium carbonate, magnesium hydroxide, aluminum hydroxide, zinc oxide, magnesium oxide, titanium oxide, silica, and talc.

As the inorganic compound based filler, calcium carbonate and barium sulfate that have an average particle diameter of 10 μm or less, in particular in the range of 0.5 to 5 μm are preferable.

Moreover, the most preferable inorganic compound based filler is an inorganic compound based filler in which a surface of an inorganic compound is treated by higher fatty acid such as stearic acid and lauric acid or metallic salt thereof in order to improve a dispersion properties with a thermoplastic resin that is a substrate.

As the thermoplastic resin (B') that is used for the air permeable film, many kinds of publicly known thermoplastic resins can be used. A polyolefin based resin such as polyethylene, polypropylene, and poly-1-butene is preferable since the resin is excellent in a water proofing property. Among them, so-called linear low density polyethylene that has a density of in the range of 0.900 to 0.940 g/cm$^3$ and is a random copolymer of ethylene and α-olefin having not less than 3 carbon atoms, preferably in the range of 4 to 10 carbon atoms, such as propylene, 1-butene, 1-heptene, 1-hexene, 1-octene, 4-methyl-1-pentene, and 1-decene, is preferable since an air permeable film to be obtained is excellent in flexibility.

The ethylene.α-olefin random copolymer is not restricted in particular. The ethylene.α-olefin random copolymer may be obtained by many kinds of publicly known catalysts such as a Ziegler catalyst and a metallocene catalyst. An ethylene.α-olefin random copolymer that can be obtained by a metallocene catalyst is preferable since the ethylene.α-olefin random copolymer gives an air permeable film excellent in mechanical strength such as tearing strength.

A small amount of high pressure low density polyethylene may be added to an ethylene.α-olefin random copolymer in order to improve an extensible property. Moreover, a small amount of polypropylene may also be added to an ethylene.α-olefin random copolymer in order to improve tensile strength of an air permeable film to be obtained.

The air permeable film in accordance with the present invention may be selected arbitrarily depending on a wide variety of applications. The thickness of the air permeable film is generally in the range of 10 to 50 g/m$^2$, preferably 12 to 40 g/m$^2$, more preferably 15 to 30 g/m$^2$. From the viewpoint of ensuring mechanical strength and obtaining a suitable water resistance for the air permeable film, the thickness of the air permeable film is preferably not less than 10 g/m$^2$. From the viewpoint of ensuring a sufficient air permeability, a thickness of the air permeable film is preferably less than 50 g/m$^2$.

EXAMPLES

The present invention will be described below in detail by examples. However, the present invention is not restricted to the examples.

The physical property values and so on in the following examples and the following comparative examples were measured by the following method.

(1) A Mass per Unit Area [g/m$^2$]

Six test pieces of 200 mm (MD)×50 mm (CD) were sampled from a non-woven fabric and/or a non-woven fabric laminate. Sampling points were arbitrary three points for each of MD and CD (total six points). A mass (g) of each sampled test piece was then measured by using the electronic pan scales (manufactured by Kensei Kogyo Co., Ltd.). The average value of the mass of each test piece was calculated. The average value obtained was converted to a mass (g) per 1 m$^2$, and the value was rounded off to one decimal place to be a mass per unit area [g/m$^2$] of each non-woven fabric sample.

(2) Maximum Point Extension Percentage [%]

Six test pieces of 200 mm (MD)×50 mm (CD) were sampled from a non-woven fabric and/or a non-woven fabric laminate. Sampling points were arbitrary three points for each of MD and CD (total six points). A tensile test of each sampled test piece was then carried out by using an universal tensile testing machine (model IM-201, manufactured by INTESCO co., Ltd.) under the conditions of a span interval 10 of 100 mm and a tension rate of 100 ram/min., and the extension percentage at the maximum strength point (maximum point extension percentage [%]) was measured. The average value of the maximum point extension percentage of the above six points (three points for each of MD and CD) was calculated, and the value was rounded off to one decimal place.

(3) Residual Strain [%]

Six test pieces of 200 mm (MD)×50 mm (CD) were sampled from a non-woven fabric and/or a non-woven fabric laminate. Sampling points were arbitrary three points for each of MD and CD (total six points). Each sampled test piece was then stretched by using the universal tensile testing machine (model IM-201, manufactured by INTESCO co., Ltd.) under the conditions of a chuck interval of 100 mm, a tension rate of 100 mm/min., and a percent of stretch of 100%, and was immediately recovered to an original length at the same rate. The strain in a recovery was measured to be a residual strain [%]. The average value of the residual strain of the above six points (three points for each of MD and CD) was calculated, and the value was rounded off to one decimal place.

(4) Locking Property

A mushroom tape (male material) of 25 mm (MD)×13 mm (CD), in which the dimension of a protrusion is 0.4 mm (average height), the size of a tip is 0.2 mm×0.3 mm (average), the number of protrusions is approximately 220/cm$^2$, and the material is polypropylene, was bonded to an end of a copying paper (strip of paper) of width 25 mm×100 mm by a pressure-sensitive adhesive double coated tape. The mushroom tape was then bonded to a non-woven fabric laminate with propriety after the evaluation of the above (3) and stretching. Sensitivity was measured five times in the case in which the mushroom tape was peeled from the non-woven fabric laminate while holding the copying paper, and the locking property was evaluated by five persons.

○: case in which four or more persons in five persons feel that a bonding was completely carried out.

Δ: case in which two or three persons in five persons feel that a bonding was completely carried out.

×: case in which one person or less in five persons feels that a bonding was completely carried out.

(5) Fuzzing

The adhesion of a non-woven fabric or a fiber to an embossing roll in the case in which the non-woven fabric and/or the non-woven fabric laminate are integrated by a heat embossing or to a forming apparatus after the integration was visually observed. In the case in which the adhesion of the non-woven fabric or the fiber is found, this is judged that there is fuzzing. In the case in which the adhesion of the non-woven fabric or the fiber is not found, this is judged that there is not fuzzing.

(6) Number of Crimps

The number of crimps was measured by the following procedures. A measuring procedure other than the procedures as described in the following was carried out according to JIS L1015.

Section lines with a space distance of 25 mm were made on a slip of a paper having a smooth surface and a gloss of a surface. A fiber was sampled from a non-woven fabric before a heat pressurizing process by using an embossing roll in a cautious manner so that a crimp property is not deteriorated. The both ends of the fiber were then bonded and fixed one by one using an adhesive with a looseness of 25±5% to the space distance.

The sample was attached one by one to a clamp of a crimp testing machine (apparatus name: TORSION BALANCE, manufactured by ASANO KIKAI Co., Ltd.), and the slip of the paper was cut. The first load (0.18 mN×number of displayed texes) was applied to the sample, and the distance (the space distance) (mm) between clamps was read at that time.

The number of crimps at that time was counted, and the number of crimps per 25 mm was obtained as an average value of 20 times. The number of crimps is determined by counting all of the peaks and troughs and dividing the number by 2.

(7) Peel Strength

Ten test pieces of 250 mm (MD)×50 mm (CD) were sampled from a non-woven fabric laminate. Sampling points were arbitrary five points for each of MD and CD (total ten points). A packing tape was bonded to the both faces of a part (approximately 2 cm from the edge in an MD direction) of a sampled test piece, and the packing tape was then manually pulled in a face direction of the test piece to peel a layer of the non-woven fabric laminate by 10 cm. The tensile test of each peeled layer was then carried out by using the universal tensile testing machine (model IM-201, manufactured by INTESCO co., Ltd.) under the conditions of a chuck interval of 100 mm and a tension rate of 100 mm/min., and the maximum strength was measured as the peel strength.

The analysis and evaluation of a thermoplastic polyurethane elastomer (TPU) that was used in examples and comparative examples were carried out according to the following methods.

(8) Solidification Starting Temperature

The solidification starting temperature was measured by using a differential scanning calorimeter (DSC220C) that was connected to a disk station SSC5200H manufactured by Seiko Instruments Inc. As a sample, a TPU of approximately 8 mg that was ground was sampled on an aluminum pan, and the aluminum pan was covered to be crimped. Alumina was sampled in a similar fashion as a reference. The sample and reference were set to the prescribed position in a cell, and were measured in a current of a nitrogen gas at a rate of flow of 40 Nml/min. The sample and reference were heated from a room temperature to a temperature of 230° C. at a rate of temperature increase of 10° C./min., were maintained at the temperature for 5 minutes, and were cooled to −75° C. at a rate of temperature decrease of 10° C./min. The starting temperature of the exothermic peak that was derived from solidification of the TPU that was recorded at that time was measured to be a solidification starting temperature (unit: ° C.).

(9) Number of Particles of Insolubles in Polar Solvents

The number of particles of insolubles in polar solvents was measured by using Multisizer II manufactured by Beckman Coulter, Inc. as a particle size distribution measuring apparatus applying the pore electrical resistance method. In a separable flask of 5 liters, dimethylacetamide (special grade product, manufactured by Wako Pure Chemical Industries, Ltd.) of 3500 g and ammonium thiocyanate (special grade product, manufactured by JUNSEI CHEMICAL CO., LTD.) of 145.83 g were weighed, and dissolved at a room temperature for 24 hours.

After that time, filtration under reduce pressure was carried out by using a membrane filter of 1 μm to obtain a reagent A. In a glass bottle of 200 cc, the reagent A of 180 g and a TPU pellet of 2.37 g were weighed, and the soluble matters in the TPU were dissolved in 3 hours to be a measuring sample. An aperture tube of 100 μm was attached to Multisizer II, a solvent in the apparatus was substituted by the reagent A, and the pressure reduction degree was adjusted to approximately 3000 mmAq. The reagent A of 120 g was weighed in a sufficiently cleaned beaker for introducing a sample, and it was confirmed that the amount of pulses that were generated in a blank measurement was 50 pieces/min or less. The optimum current value and gain were specified according to a manual, and a calibration was carried out by using an uncrosslinked polystyrene standard particle of 10 μm. The measurement was carried out for 210 seconds after the reagent A of 120 g and the measuring sample of approximately 10 g were weighed in a sufficiently cleaned beaker for introducing a sample. The value that was obtained by dividing the number of particles that were counted in the measurement by the weight of TPU that was sucked by the aperture tube was made to be the number of particles (unit: pieces/g) of insolubles in polar solvents in the TPU. The weight of TPU was calculated by the following expression.

$$\text{Weight of TPU} = \{(A/100) \times B/(B+C)\} \times D$$

In the above expression, A is the TPU concentration (% by weight) of the measuring sample, B is the weight (g) of the measuring sample that was weighed in a beaker, C is the weight (g) of the reagent A that was weighed in a beaker, and D is the amount of solution (g) that was sucked by the aperture tube in the measurement (for 210 seconds).

(10) Ratio of Heat of Fusion of a Hard Domain

A ratio of heat of fusion of a hard domain was measured by using the differential scanning calorimeter (DSC220C) that was connected to the disk station SSC5200H manufactured by Seiko Instruments Inc. As a sample, a TPU of approximately 8 mg that was ground was sampled on an aluminum pan, and the aluminum pan was covered to be crimped. Alumina was sampled in a similar fashion as a reference. The sample and reference were set to the prescribed position in a cell, and were measured in a current of a nitrogen gas at a rate of flow of 40 Nml/min. The sample and reference were heated from a room temperature to a temperature of 230° C. at a rate of temperature increase of 10° C./min. At this time, a total sum (a) of a heat of fusion that is obtained from an endothermic peak in which a peak temperature is in the range of 90 to 140° C. and a total sum (b) of a heat of fusion that is obtained from an endothermic peak in which a peak temperature is in the range of more than 140 to 220° C. were obtained, and the ratio of heat of fusion (unit: %) of a hard domain was obtained by the following expression.

Ratio of heat of fusion (%) of a hard domain=$a/(a+b) \times 100$

(11) Melt Viscosity at 200° C. (Hereafter Simply Referred to as a "Melt Viscosity")

The melting viscosity of the TPU (unit: unit: Pa·s) was measured by using CAPILOGRAPH (model 10, manufactured by TOYO SEIKI Co., Ltd.) under the conditions of a temperature of 200° C. and a shear rate of 100 sec$^{-1}$. A nozzle having a length of 30 mm and a diameter of 1 mm was used.

(12) Moisture Value of TPU

The moisture amount (unit: ppm) of the TPU was measured by a combination of a moisture amount measuring apparatus (AVQ-5S, manufactured by Hiranuma Sangyo Corporation) and a moisture vaporization apparatus (EV-6, manufactured by Hiranuma Sangyo Corporation). A TPU pellet of approximately 2 g that was weighed in a heating sample pan was introduced to a heating furnace at a temperature of 250° C., vaporized moisture was introduced to a titration cell of the moisture amount measuring apparatus in which residual moisture was removed in advance, and a titration was carried out by using Karl Fischer reagent. In the case in which the change of an electric potential for a titration electrode, which is accompanied with the change of a moisture amount in a cell, did not occur for 20 seconds, a titration was judged to be completed.

(13) Shore A Hardness

The hardness of the TPU was measured under the conditions of a temperature of 23° C. and a relative humidity of 50% according to the method as described in JIS K-7311. A durometer of a type A was used.

Production Example 1 of a Thermoplastic Polyurethane Elastomer

Diphenylmethane diisocyanate (hereafter referred to as MDI) was charged to a tank A in a nitrogen atmosphere, and the temperature was adjusted at 45° C. while stirring in such a manner that an air bubble is not included.

Polyester polyol having a number average molecular weight of 2000 (trade name: TAKELAC U2024, manufactured by MITSUI TAKEDA CHEMICALS, INC.) of 628.6 parts by weight, IRGANOX 1010 of 2.21 parts by weight, and 1,4-butanediol of 77.5 parts by weight were charged to a tank B in a nitrogen atmosphere, and the temperature was adjusted at 95° C. while stirring. This blended material is referred to as a polyol solution 1.

The amount of a hard segment that is calculated from those reaction raw materials was 37.1% by weight.

The MDI and the polyol solution 1 were then quantitatively introduced at a rate of flow of 17.6 kg/h and 42.4 kg/h, respectively, to a high speed stirring machine (SM40) that was adjusted at 120° C. through a solution sending line via a gear pump and a flow meter. The MDI and the polyol solution 1 were stirred and mixed at 2000 rpm for 2 minutes, and were introduced to a static mixer. In the static mixer section, the first to third static mixers (a temperature of 230° C.) in which three static mixers having a pipe length of 0.5 m and an inner diameter of 20 mmϕ were connected, the fourth to sixth static mixers (a temperature of 220° C.) in which three static mixers having a pipe length of 0.5 m and an inner diameter of 20 mmϕ were connected, the seventh to twelfth static mixers (a temperature of 210° C.) in which six static mixers having a pipe length of 1.0 m and an inner diameter of 34 mmϕ were connected, and the thirteenth to fifteenth static mixers (a temperature of 200° C.) in which three static mixers having a pipe length of 0.5 m and an inner diameter of 38 mmϕ were connected, were connected in series.

A reaction product that was flown out from the fifteenth static mixer was injected via a gear pump to a single axis extrusion machine (a diameter of 65 mmϕ and a temperature in the range of 180 to 210° C.) provided with a polymer filter (manufactured by NAGASE & CO., LTD., trade name: DENAFILTER) at the end thereof, and was extruded from a strand die. After water cooling, the reaction product was continuously pelletized by a pelletizer. A pellet that was obtained was then charged into a drying machine, and was dried at 100° C. for 8 hours to obtain a thermoplastic polyurethane elastomer having a moisture value of 40 ppm. The thermoplastic polyurethane elastomer was continuously extruded by a single axis extrusion machine (a diameter of 50 mmϕ and a temperature in the range of 180 to 210° C.), and was pelletized. A pellet that was obtained was dried again at 100° C. for 7 hours to obtain a thermoplastic polyurethane elastomer (A-1) having a moisture value of 57 ppm.

The thermoplastic polyurethane elastomer (A-1) had a solidification starting temperature of 103.7° C., a number of particles of insolubles in polar solvents of one and half millions/g, a hardness of a test piece that was prepared by an injection molding of 86 A, a melting viscosity at 200° C. of 1900 Pa·s, and a ratio of heat of fusion of a hard domain of 35.2%.

Example 1

Preparation of a Thermoplastic Resin Composition for a Spunbonded Non-Woven Fabric A propylene homopolymer (hereafter referred to as "PP-1") of 96% by weight, whose MFR (according to ASTM D1238, and measured at a temperature of 230° C. and a load of 2.16 kg) was 60 g/10 min, density was 0.91 g/cm$^3$, melting point was 160° C., and Mw/Mn=2.9, was mixed with a high density polyethylene (hereafter referred to as "HDPE") of 4% by weight, whose MFR (according to ASTM D1238, and measured at a temperature of 190° C. and a load of 2.16 kg) was 5 g/10 min, density was 0.97 g/cm$^3$, and melting point was 134° C., to prepare a thermoplastic resin composition (B-1).

Production of a Non-Woven Fabric Laminate

The thermoplastic polyurethane elastomer (A-1) and the thermoplastic resin composition (B-1) were independently molten by using an extrusion machine of 75 mmφ and an extrusion machine of 50 mmφ, respectively. Melt spinning was then carried out by using a spunbonded non-woven fabric forming machine provided with a spinneret (a length in a direction perpendicular to a flow direction of the machine on a collection face: 800 mm) according to a spunbonding method under the conditions of a resin temperature and a die temperature of both 210° C., a temperature of a cooling air of 20° C., and a wind velocity of a stretching air of 3750 m/min. A web comprising mixed continuous fibers including a continuous fiber A comprising A-1 and a continuous fiber B comprising B-1 was accumulated on a collection face to obtain a web comprising mixed fibers whose fiber A:fiber B was 41:59 (% by weight). The spinneret was provided with a nozzle pattern in which a discharge hole for A-1 and a discharge hole for B-1 were arranged in alternate shifts, and the nozzle diameter for A-1 (fiber A) was 0.75 mmφ and the nozzle diameter for B-1 (fiber B) was 0.6 mmφ. The pitch of the nozzle was 8 mm in a vertical direction and 11 mm in a horizontal direction, and the ratio of the number of nozzles was a nozzle for the fiber A: a nozzle for the fiber B=1:1.45. A single-hole discharge rate of the fiber A was 0.73 g/(min·hole), and a single-hole discharge rate of the fiber B was 0.73 g/(min·hole).

The web comprising mixed continuous fibers that were accumulated was subjected to a nip roller (a linear pressure of 10 kg/cm) that was disposed on the belt and that was coated with a non-adhesive material to obtain a mixed fiber spunbonded non-woven fabric. The mass per unit area of the mixed fiber spunbonded non-woven fabric that was obtained was 30 g/m². The fiber diameters of the web comprising mixed continuous fibers that were accumulated was 29.2μm for the larger fiber diameter and 21.0 μm for the smaller fiber diameter. Consequently, the fiber diameter of A-1 and the fiber diameter of B-1 were considered to be 29.2 μm and 21.0 μm, respectively.

The mixed fiber spunbonded non-woven fabric was then sent on a moving belt. A propylene ethylene random copolymer (hereafter referred to as "PP-2"), whose MFR (according to ASTM D1238, and measured at a temperature of 230° C. and a load of 2.16 kg) was 60 g/10 min, density was 0.91 g/cm³, melting point was 138° C., and Mw/Mn=3.0, was molten by an extrusion machine (75 mmφ), PP-1 was molten by an extrusion machine (50 mmφ), and a parallel type composite fiber having a weight ratio of PP-2:PP-1=80:20 was molten and extruded. A crimped fiber non-woven fabric (a spunbonded non-woven fabric) having a mass per unit area of 30 g/m² was thus accumulated on a moving belt, and a non-woven fabric laminate was obtained by use of a nip roller (a linear pressure of 10 kg/cm).

The fiber diameter of the fiber was 20.2 μm, and the number of crimps was not less than 29/25 mm.

The laminate was peeled from the moving belt. The emboss pattern of the laminate that was obtained by the process had an area ratio of 18%, and an emboss area of 0.41 mm². The two layers of the laminate were integrated by a heat embossing under the conditions of a heating temperature of 110° C. and a linear pressure of 30 kg/cm, and a non-woven fabric laminate that had a mass per unit area of 60 g/m² and that comprised a mixed fiber spunbonded non-woven fabric/a crimped fiber non-woven fabric was obtained.

The existence or nonexistence of "a break in a stretching process" and the existence or nonexistence of "a crease in a stretching process" of the non-woven fabric laminate that was obtained were visually evaluated (similarly carried out in the following examples and the following comparative examples). Moreover, the existence or nonexistence of peeling for the laminate was visually evaluated after the process of the above described (3) Residual strain was repeated 20 times for an extension (repeated extension at 20 times).

Moreover, a spunbonded non-woven fabric of 18 g/m² was separately produced by using only the thermoplastic resin composition (B-1), and the maximum point extension percentage [%] was measured by the method as described above. As a result, the maximum point extension percentage was 172% (MD) and 150% (CD), and the residual strain was 96% (MD) and 98% (CD). The non-woven fabric laminate that was obtained was evaluated by the method as described above. The above described (4) Locking property was evaluated on a face on the side of a crimped spunbonded non-woven fabric layer. The evaluation results are listed in Table 1.

Example 2

A web comprising mixed fibers having a mass per unit area of 40 g/m² was obtained as the same manner as in Example 1, except that the single-hole discharge rate of the fiber A was 0.44 g/(min·hole), the single-hole discharge rate of the fiber B was 0.92 g/(min·hole), and the fiber A:the fiber B was 25:75 (% by weight).

A crimped fiber spunbonded non-woven fabric having a mass per unit area of 20 g/m² was then laminated on the web. The two layers were integrated by an embossing to obtain a non-woven fabric laminate that had a mass per unit area of 60 g/m² and that comprised a mixed fiber spunbonded non-woven fabric/a crimped fiber non-woven fabric.

The non-woven fabric laminate that was obtained was evaluated by the method as described above. The above described (4) Locking property was evaluated on a face on the side of a crimped spunbonded non-woven fabric layer. The evaluation results are listed in Table 1.

Example 3

A web comprising mixed fibers having a mass per unit area of 20 g/m² was obtained as the same manner as in Example 1, except that the single-hole discharge rate of the fiber A was 1.1 g/(min·hole), the single-hole discharge rate of the fiber B was 0.5 g/(min·hole), and the fiber A:the fiber B was 60:40 (% by weight).

A crimped fiber spunbonded non-woven fabric having a mass per unit area of 40 g/m² was then laminated on the web. The two layers were integrated by an embossing to obtain a non-woven fabric laminate that had amass per unit area of 60 g/m² and that comprised a mixed fiber spunbonded non-woven fabric/a crimped fiber non-woven fabric.

The non-woven fabric laminate that was obtained was evaluated by the method as described above. The above described (4) Locking property was evaluated on a face on the side of a crimped spunbonded non-woven fabric layer. The evaluation results are listed in Table 1.

Comparative Example 1

A non-woven fabric laminate that had a mass per unit area of 60 g/m² and that comprised a mixed fiber spunbonded non-woven fabric/a non-crimped fiber non-woven fabric was obtained as the same manner as in Example 1, except that PP-2 was used singly instead of the crimped fiber spunbonded non-woven fabric, and a spunbonded non-woven fabric (a non-crimped fiber) made by an extrusion at a discharge rate of approximately 1.25 times was laminated.

The non-woven fabric laminate that was obtained was evaluated by the method as described above. The evaluation results are listed in Table 2.

Comparative Example 2

A non-woven fabric laminate that had a mass per unit area of 60 g/m² and that comprised a mixed fiber spunbonded non-woven fabric/a non-crimped fiber non-woven fabric was obtained as the same manner as in Comparative example 1, except that a spunbonded non-woven fabric (a non-crimped fiber) comprising the thermoplastic resin composition (B-1) was laminated instead of the spunbonded non-woven fabric (a non-crimped fiber) comprising PP-2 singly.

The non-woven fabric laminate that was obtained was evaluated by the method as described above. The above described (4) Locking property was evaluated on a face on the side of a spunbonded non-woven fabric layer comprising a non-crimped fiber. The evaluation results are listed in Table 2.

Comparative Example 3

According to the method described in Example 2, a mixed fiber spunbonded non-woven fabric whose fiber A:fiber B was 25:75 (% by weight) and mass per unit area was 60 g/m² was obtained, and the mixed fiber non-woven fabric of a single layer was embossed. The mixed fiber spunbonded non-woven fabric that was obtained was evaluated by the method as described above. The evaluation results are listed in Table 2.

Comparative Example 4 non-woven fabric laminate that had a mass per unit area of 60 g/m² and that comprised a non mixed fiber spunbonded non-woven fabric/a crimped fiber non-woven fabric was obtained as the same manner as in Example 1, except that a spunbonded non-woven fabric that comprised the thermoplastic resin composition (B-1) and had a mass per unit area of 30 g/m² was used instead of the mixed fiber spunbonded non-woven fabric.

The non-woven fabric laminate that was obtained was evaluated by the method as described above. The above described (4) Locking property was evaluated on a face on the side of a spunbonded non-woven fabric layer comprising a crimped fiber. The evaluation results are listed in Table 2.

Comparative Example 5

A discharge of B-1 in Example 1 was stopped, and a spunbonded non-woven fabric comprising only A-1 having a mass per unit area of 15 g/m² was obtained. The crimped fiber non-woven fabric that was used in Example 1 was then tried to be laminated for an embossing integration. However, the spunbonded non-woven fabric was wound in embossing, and it was impossible to obtain a non-woven fabric laminate.

Example 4

According to the method as described in Example 1, a mixed fiber spunbonded non-woven fabric was obtained whose fiber A:fiber B was 41:59 (% by weight) and mass per unit area was 15 g/m². The crimped fiber non-woven fabric having a mass per unit area of 30 g/m² that was used in Example 1 was then laminated, and the mixed fiber spunbonded non-woven fabric whose fiber A:fiber B was 41:59 and mass per unit area was 15 g/m² was laminated on the crimped fiber non-woven fabric. The mixed fiber spunbonded non-woven fabric and the crimped fiber non-woven fabric were embossed by the method as described in Example 1 to obtain a non-woven fabric laminate that had a mass per unit area of 60 g/m² and that comprised a mixed fiber spunbonded non-woven fabric/a crimped fiber non-woven fabric/a mixed fiber spunbonded non-woven fabric.

The non-woven fabric laminate that was obtained was evaluated by the method as described above. The evaluation results are listed in Table 3.

Example 5

A crimped fiber non-woven fabric comprising a parallel type composite fiber having a mass per unit area of 15 g/m² and weight ratio of PP-2:PP-1=80:20 was obtained as the same manner as described in Example 1. The mixed fiber spunbonded non-woven fabric whose fiber A:fiber B was 41:59 (% by weight) and mass per unit area was 30 g/m² was then laminated by the method as described in Example 1. The crimped fiber non-woven fabric having a mass per unit area of 15 g/m² was then laminated on the mixed fiber spunbonded non-woven fabric. The mixed fiber spunbonded non-woven fabric and the crimped fiber non-woven fabric were embossed by the method as described in Example 1 to obtain a non-woven fabric laminate that had a mass per unit area of 60 g/m² and that comprised a crimped fiber non-woven fabric/a mixed fiber spunbonded non-woven fabric/a crimped fiber non-woven fabric.

The non-woven fabric laminate that was obtained was evaluated by the method as described above. The evaluation results are listed in Table 3.

Comparative Example 6

A spunbonded non-woven fabric comprising only A-1 as described in Comparative example 5 was used in stead of the mixed fiber spunbonded non-woven fabric that was used in Example 5, and a non-woven fabric laminate that had a mass per unit area of 60 g/m² and that comprised a crimped fiber non-woven fabric/spunbonded non-woven fabric/a crimped fiber non-woven fabric was obtained.

The non-woven fabric laminate that was obtained was evaluated by the method as described above. The above described (4) Locking property was evaluated on a face on the side of a crimped fiber spunbonded non-woven fabric layer. The evaluation results are listed in Table 3.

TABLE 1

|  | Example 1 | Example 2 | Example 3 |
|---|---|---|---|
| Break in a stretching process | None | None | None |
| Crease after a stretching process | None | None | None |
| Residual strain MD | 20 | 21 | 20 |
| Residual strain CD | 27 | 28 | 27 |
| Maximum point extension percentage MD | 114 | 119 | 110 |
| Maximum point extension percentage CD | 109 | 111 | 108 |
| Repeated extension at 20 times | None | None | None |
| Locking property | Confirmed | Confirmed | Confirmed |

TABLE 2

|  | Comparative example 1 | Comparative example 2 | Comparative example 3 | Comparative example 4 | Comparative example 5 |
|---|---|---|---|---|---|
| Break in a stretching process | Generated | None | None | None | Formation impossible |
| Crease after a stretching process | — | Confirmed | None | None | |
| Residual strain MD | — | 23 | 18 | 95 | |
| Residual strain CD | — | 31 | 25 | 97 | |
| Maximum point extension percentage MD | — | 158 | 190 | 108 | |
| Maximum point extension percentage CD | — | 162 | 198 | 113 | |
| Repeated extension at 20 times | — | None | None | None | |
| Locking property | — | Small | Small | Small | |

TABLE 3

|  | Example 4 | Example 5 | Example 6 |
|---|---|---|---|
| Break in a stretching process | None | None | None |
| Crease after a stretching process | None | None | None |
| Residual strain MD | 19 | 20 | 21 |
| Residual strain CD | 26 | 26 | 27 |
| Maximum point extension percentage MD | 114 | 107 | 112 |
| Maximum point extension percentage CD | 111 | 113 | 113 |
| Repeated extension at 20 times | None | None | Peeled |
| Locking property | None | Confirmed | Confirmed |

Example 6

A crimped fiber non-woven fabric comprising a parallel type composite fiber having a mass per unit area of 15 g/m² and a weight ratio of PP-2:PP-1=80:20 was obtained by the method as described in Example 1. A spunbonded non-woven fabric (C-1) in which only the thermoplastic resin composition (B-1) was used was then laminated as an intermediate layer between the crimped non-woven fabric and the mixed fiber non-woven fabric. According to the method as described in Example 1, the mixed fiber spunbonded non-woven whose fiber A:fiber B was 41:59 (% by weight) and mass per unit area was 30 g/m² was then laminated. The non-woven fabric laminate that had a mass per unit area of 55 g/m² and that comprised a crimped fiber non-woven fabric/a spunbonded non-woven fabric (C-1)/a mixed fiber spunbonded non-woven fabric was then obtained by the method as described in Example 1.

There was no break in a stretching process and no crease after a stretching process. The maximum point extension percentage was 113 for MD and 104 for CD. The residual strain was 35 for MD and 43 for CD.

In the case in which the force of 1.0 N or larger was applied to the obtained non-woven fabric laminate by the method as described in the above (13) Peel strength, the non-woven fabric laminate was not peeled. The non-woven fabric laminate was thus improved in the peel strength.

Example 7

A non-woven fabric laminate that had a mass per unit area of 55 g/m² and that comprised a crimped fiber non-woven fabric/a composite fiber spunbonded non-woven fabric (C-2)/a mixed fiber spunbonded non-woven fabric was obtained as the same manner as in example 6, except that a spunbonded non-woven fabric (C-2) comprising a concentric type composite fiber (PP-1 is a core) having a weight ratio of PP-2:PP-1=20:80 was used instead of C-1 as an intermediate layer.

There was no break in a stretching process and no crease after a stretching process. The maximum point extension percentage was 108 for MD and 100 for CD. The residual strain was 38 for MD and 45 for CD. In the case in which the force of 1.0 N or larger was applied to the obtained non-woven fabric laminate by a method as described in Example 6, the non-woven fabric laminate was not peeled. The non-woven fabric laminate was thus improved in the peel strength.

Example 8

A non-woven fabric laminate that had a mass per unit area of 50 g/m² and that comprised a crimped fiber non-woven fabric/a melt blow non-woven fabric (C-3)/a mixed fiber spunbonded non-woven fabric was obtained as the same manner as in Example 6, except that a melt blow non-woven fabric (C-3) in which PP-1 was adopted was used instead of C-1 as an intermediate layer.

There was no break in a stretching process and no crease after a stretching process. The maximum point extension percentage was 108 for MD and 104 for CD. The residual strain was 22 for MD and 30 for CD.

In the case in which a force of 1.0 N or larger was applied to the obtained non-woven fabric laminate by a method equivalent to that as described in Example 6, the non-woven fabric laminate was not peeled. The non-woven fabric laminate was thus improved in the peel strength.

TABLE 4

|  | Example 6 | Example 7 | Example 8 |
|---|---|---|---|
| Break in a stretching process | None | None | None |
| Crease after a stretching process | None | None | None |
| Residual strain MD | 35 | 38 | 22 |
| Residual strain CD | 43 | 45 | 30 |
| Maximum point extension percentage MD | 113 | 108 | 108 |
| Maximum point extension percentage CD | 104 | 100 | 104 |

TABLE 4-continued

| | Example 6 | Example 7 | Example 8 |
|---|---|---|---|
| Repeated extension at 20 times | None | None | None |
| Locking property | Confirmed | Confirmed | Confirmed |

INDUSTRIAL APPLICABILITY

The non-woven fabric laminate of the present invention is excellent in stretchability, flexibility, moisture permeability, air permeability, a fuzzing resistant property, and strength, and is provided with a locking property for a mechanical fastening female material as needed. By utilizing such characteristics, the non-woven fabric laminate of the present invention can be suitably used for a sanitary material, a medical material, an industrial material, and other materials.

Specifically, there can be mentioned for instance an absorbent article such as a disposable diaper and a menstrual sanitary product as a sanitary material. The non-woven fabric laminate of the present invention can be suitably used for regions such as a top sheet, a back sheet, a west band (an extension tape and a side flap), a fastening tape, a stereo gather, and a leg cuff for a developing type disposable diaper or a pants type disposable diaper, and for regions such as a side panel for a pants type disposable diaper. Moreover, the non-woven fabric laminate of the present invention can be suitably used for regions such as a top sheet, a back sheet, a wing, and a side leak prevention cuff for a sanitary napkin. By using the article in accordance with the present invention for the above regions, the regions can follow the movement of a wearer and fit the body of a wearer. Moreover, a comfortable state can be maintained even in being worn, and a thin shape, a reduction in weight, and a compactification of a package can also be expected.

As a medical material for which an article in accordance with the present invention can be used, there can be mentioned for instance a base cloth of a fomentation. The base cloth in accordance with the invention has a suitable stretchability and a pleasant texture, which impart a following property to the movement of a body and a skin care property, whereby can also be expected to contribute to a healing effect. Similarly, for a material for a medical treatment of an injury, since an article in accordance with the present invention is provided with a suitable stretchability and a high adhesion property to a diseased part, it is expected to improve a recovery of a wound. Moreover, since a mixed fiber non-woven fabric laminate in accordance with the present invention is provided with a suitable air permeability similarly to a normal non-woven fabric and further with an excellent stretchability, it is expected that the mixed fiber non-woven fabric laminate in accordance with the present invention can be used for a part in which an air permeability and a stretchability are required such as a disposable operating gown, a cap, and a movable indirect part such as an arm, an elbow, a shoulder, and a sleeve of a rescue gown.

The invention claimed is:

1. A female material of mechanical fastening, wherein the female material comprises a non-woven fabric laminate comprising a mixed fiber spunbonded non-woven fabric and a non-woven fabric comprising a crimped fiber, the mixed fiber spunbonded non-woven fabric comprising a continuous fiber of a thermoplastic polyurethane based elastomer in the range of 10 to 90% by weight and a continuous fiber of a thermoplastic resin (B) in the range of 90 to 10% by weight (where the thermoplastic polyurethane based elastomer+(B)=100% by weight), the non-woven fabric comprising a crimped fiber being laminated on at least one face of the mixed fiber spunbonded non-woven fabric, wherein the crimped fiber is an eccentric core-in-sheath crimped fiber or a parallel type crimped fiber which comprises a first component comprising a propylene-α-olefin copolymer having a melting point (Tm) of 150° or less and a second component comprising a propylene based polymer having a melting point (Tm) of 155° C. or higher, and the ratio (the mass ratio) of the first component to the second component is in the range of 50/50 to 95/5.

2. The female material of mechanical fastening as defined in claim 1, wherein a spunbonded non-woven fabric comprising the continuous fiber of the thermoplastic resin (B) has a maximum point extension percentage of not less than 50%.

3. The female material of mechanical fastening as defined in claim 1, wherein the continuous fiber of the thermoplastic resin (B) is a continuous fiber of a propylene based polymer.

4. The female material of mechanical fastening as defined in claim 1, wherein the crimped fiber is a continuous fiber.

5. The female material of mechanical fastening as defined in claim 1, wherein the crimped fiber is a crimped fiber provided with a modified cross section.

6. The female material of mechanical fastening as defined in claim 1, wherein the non-woven fabric comprising a crimped fiber has a maximum point extension percentage of not less than 50%.

* * * * *